US006906535B2

(12) United States Patent
Murphy, Jr. et al.

(10) Patent No.: US 6,906,535 B2
(45) Date of Patent: Jun. 14, 2005

(54) METHOD FOR CHARACTERIZING WATER-IN-OIL EMULSIONS USING ELECTRICAL WAVE FORMS

(75) Inventors: Robert J. Murphy, Jr., Kingwood, TX (US); Dale E. Jamison, Humble, TX (US)

(73) Assignee: Halliburton Energy Services, Inc., Duncan, OK (US)

( * ) Notice: Subject to any disclaimer, the term of this patent is extended or adjusted under 35 U.S.C. 154(b) by 105 days.

(21) Appl. No.: 10/137,681

(22) Filed: May 2, 2002

(65) Prior Publication Data

US 2003/0206024 A1 Nov. 6, 2003

(51) Int. Cl.$^7$ .......................... G01R 27/08; G01V 3/18
(52) U.S. Cl. ...................................... 324/713; 324/366
(58) Field of Search ................................ 324/698, 346, 324/323, 324, 333, 338, 351, 355, 356, 368, 369, 372, 303, 339, 366, 713, 541, 551, 553, 453; 175/65, 70

(56) References Cited

U.S. PATENT DOCUMENTS

| | | | | |
|---|---|---|---|---|
| 4,008,922 A | * | 2/1977 | Kallin et al. ................. 299/13 |
| 4,134,799 A | * | 1/1979 | Allen et al. ............... 205/793.5 |
| 4,315,421 A | * | 2/1982 | Wilson .......................... 72/42 |
| 4,481,121 A | * | 11/1984 | Barthel ....................... 507/138 |
| 4,663,076 A | * | 5/1987 | Clapper et al. ............... 516/27 |
| 5,345,819 A | * | 9/1994 | Dearing, Jr. ............. 73/152.23 |
| 5,811,841 A | * | 9/1998 | Ganguly et al. ............ 257/113 |
| 6,006,831 A | * | 12/1999 | Schlemmer et al. ... 166/250.01 |
| 6,154,710 A | * | 11/2000 | Kobayashi et al. ........... 702/65 |
| 6,335,100 B1 | * | 1/2002 | Tominaga et al. ....... 428/474.4 |
| 6,509,738 B1 | * | 1/2003 | Minerbo et al. ............ 324/339 |
| 6,525,003 B2 | * | 2/2003 | Schlemmer et al. ........ 507/103 |

FOREIGN PATENT DOCUMENTS

| | | | |
|---|---|---|---|
| JP | 411323926 A | * 11/1999 | ............. E02D/5/80 |

OTHER PUBLICATIONS

Muhr et al., New Ways of Disruptive Discharge Recognition in Insulation Testing Devices, Jun. 21, 2000, 0–7803–5459–1/99/$10.00 1999IEEE, 4 pages.*

Fink et al., Standard Handbook for Electrical Engneers, 1969, McGraw–Hill Inc., Tenth Edition, 3 pages.*

Abstract No. XP–002261885 entitled Determination of type of emulsion stabilizer—by measuring current passing through system under specified voltage, and using its change as indicator, date Aug. 15, 1990.

Abstract No. XP–002261886 entitled "Device determining electrical stability of water–in–oil emulsions," Jun. 27, 2002.

"Recommended Practice Standard Procedure for Field Testing Oil–Based Drilling Fluids", API Recommended Practice 13B–2, Third Edition, Feb. 1998.

SPE/IADC 16077, "Investigation of teh Electrical Stability Test for Oil Muds," A. Ali, D.D. Schmidt, and J. Harvey III (1987).

* cited by examiner

*Primary Examiner*—Edward Lefkowitz
*Assistant Examiner*—Hoai-An D. Nguyen
(74) *Attorney, Agent, or Firm*—Craig W. Roddy; Karen B. Tripp

(57) ABSTRACT

A method is provided for characterizing emulsion stability to evaluate suitability of the emulsion for use as a drilling fluid in drilling subterranean boreholes. The method provides a supplement or alternative to the standard method of determining Electrical Stability of the emulsion. In the method of the invention, Breakdown Energy is calculated. Breakdown Energy can be measured at the same test point as Electrical Stability. A digital storage oscilloscope and a computer are used in addition to an electrical stability meter.

17 Claims, 2 Drawing Sheets

METHOD FOR CHARACTERIZING WATER-IN-OIL EMULSIONS USING ELECTRICAL WAVE FORMS

BACKGROUND OF THE INVENTION

1. Field of the Invention

The present invention relates to methods and apparatuses for characterizing or evaluating the strength or effectiveness of oil based drilling fluids for use in drilling wellbores in subterranean formations. The invention relates particularly to methods and apparatuses for characterizing water-in-oil or invert emulsion fluids for use in drilling wellbores in hydrocarbon-bearing subterranean formations.

2. Description of Relevant Art

The Electrical Stability meter (ES), such as the FANN 23D (FIG. 3) available from Halliburton Energy Services, Inc. in Houston, Tex., has been used to characterize invert emulsion oil-based drilling fluids for many years. The first patent issued for an ES meter was U.S. Pat. No. 2,859,404, issued Nov. 4, 1958 to B. C. Crittendon. When diesel-based drilling fluids were the dominant oil-based fluids, the ES meter was a particularly useful diagnostic tool. The higher the ES voltage measured for the fluid, the stronger or harder to break would be the emulsion created with the fluid and consequently the better the fluid would likely be as a drilling fluid.

Invert emulsion oil-based drilling fluids are stabilized by the addition of emulsifiers. The water phase is usually about 5% to about 40% of the total liquid volume and is usually comprised of (but not limited to) calcium chloride brine. The brine concentration is adjusted to control the water exchange between the drilling fluid and the formation being drilled and to aid in formation stability. If the formulation of the invert emulsion drilling fluid becomes unbalanced, due to, for example (without limitation), contamination, improper product additions, or thermal degradation, the emulsion can flip. When such flipping happens, the water becomes the continuous phase, and can the cause the solids in the drilling fluid to become water wet. Such wetting requires expensive remedial action and can lead to the loss of the well.

The strong electric field induced by the ES meter causes tiny water droplets in the drilling fluid to orient and coalesce to form conductive bridges between the faces of the electrodes of the ES meter probe. Solid materials in the drilling fluid may aid or interfere with formation of the conductive bridge. (See SPE/IADC 16077, "Investigation of the Electrical Stability Test for Oil Muds", A. Ali, D. D. Schmidt and J. Harvey III, (1987)). These solid materials typically include, for example, weight material that is added to increase the density, drill cuttings or drilled formation solids, and colloidal solids added to control the viscosity and suspension properties of the drilling fluid.

The electrical stability test method specified by the American Petroleum Institute is "Recommended Practice Standard Procedure for Field Testing Oil-Based Drilling Fluids", API Recommended Practice 13B-2, Third Edition, February 1998 ("the API Procedure"), incorporated herein by reference. Paragraph 8.1.1 states: "The electrical stability (ES) of an oil-based drilling fluid mud is a property related to its emulsion stability and oil-wetting capability. ES is determined by applying a voltage-ramped, sinusoidal electrical signal across a pair of parallel flat-plate electrodes immersed in the mud. The resulting current remains low until a threshold voltage is reached, whereupon the current rises very rapidly. This threshold voltage is referred to as the ES ("the API ES") of the mud and is defined as the voltage in peak volts-measured when the current reaches 61 $\mu$A." This API Procedure also specifies the other instrument parameters that must be controlled to make repeatable measurements. Such parameters include the waveform, AC frequency (340±10 Hz), voltage ramp rate, break current and electrode diameter and spacing (gap).

The ES meter has evolved over the years since the first instruments were introduced. Additions such as automatic voltage ramps, superior electronics and electrode design improvements have been made. However, the composition of drilling fluids has also evolved. Increasingly, oil-based drilling fluids formulated using mineral oils, synthetics (or synthetic oils), and esters instead of diesel oil are being used. ES voltages that have been good indicators of emulsion performance with diesel oil-based fluids are unobtainable with many of these newer or alternative invert emulsion based fluids. ES voltages for such invert emulsion based fluids currently range from about 100 V to over about 1000 V. Thus, with such a broad "acceptable" range, ES measurements with an ES meter no longer provide the precise or dependable information needed for practical judgments regarding emulsion performance, quality or stability.

SUMMARY OF THE INVENTION

The present invention provides a method for characterizing or evaluating emulsion stability, and consequently emulsion quality and performance. In the method of the invention, the ES of the emulsion may be determined in a standard or accepted manner as prescribed in the API Procedure. However, in addition to or as an alternative to noting the threshold voltage or API ES for the emulsion, the current and voltage waveforms just prior to the breakdown event are analyzed. As used herein, the term "API break event," "API breakdown event," or "API breakdown" shall mean the time when a voltage-ramped sinusoidal electrical signal across a pair of parallel flat-plate electrodes immersed in the emulsion reaches a threshold voltage whereupon the current reaches 61 $\mu$A. That is, the term "API break event," "API breakdown event," or "API breakdown" refers to the point at which the API ES is or would be measured according to the API Procedure. The voltage waveform is generally or typically controlled by the ES meter or instrument for measuring the ES; thus, the current waveform is examined in relation to the voltage waveform. In the time leading up to the API breakdown event, the current waveform for different oil-based drilling fluids can vary from a sharp spike (exemplified in FIG. 1) to a smooth sinusoidal waveform (exemplified in FIG. 2).

The term "'true' break event," "'true' breakdown event," or "'true' breakdown" as used herein (without reference to API) shall mean the time when a voltage-ramped sinusoidal electrical signal across a pair of parallel flat-plate electrodes immersed in the emulsion reaches a threshold voltage whereupon the current starts to rise rapidly and disproportionally faster than the voltage waveform. This definition of the term more accurately describes the point of catastrophic failure of the emulsion than the API definition. The API breakdown and the "true" breakdown are effectively the same for emulsions that give waveforms of a spiky nature (exemplified in FIG. 1). However, the smooth sinusoidal waveform (exemplified in FIG. 2) implies that the emulsion has not truly failed at the API defined current level. If the voltage ramp had been allowed to continue, the emulsion would have probably experienced a true failure or "true" breakdown, with the characteristic rapid increase of current.

When the term "breakevent," "breakdown event" or "breakdown" are used herein without designation as to whether the API definition or the "true" definition is intended, it shall be understood that the terms are interchangeable for the purposes of the invention, that is, are both workable in the invention, even though the events are not always the same.

Preferably, the waveforms are analyzed by sampling both current and voltage waveforms rapidly, from the time the voltage waveform crosses the zero point, to the moment of breakdown, preferably "true" breakdown although API breakdown may be used. At each time interval the voltage and current values are multiplied together to obtain the instantaneous power. Then, each of the instantaneous power values is multiplied by the sample interval time and is summed to obtain the energy expended by the instrument in the cycle leading up to the breakdown event. This process can be expressed symbolically by the following equation:

$$\text{Breakdown Energy} \cong \sum_{k=1}^{n} i_k \times E_k \times (t_k - t_{k-1})$$

Where:
$i_k$=current
$E_k$=Voltage
$t_k$=Time
n=number of measurements

The greater the Breakdown Energy, the stronger the emulsion, indicating a likely better drilling fluid than fluids with lesser Breakdown Energies.

DETAILED DESCRIPTION OF PREFERRED EMBODIMENTS

Figure 1:
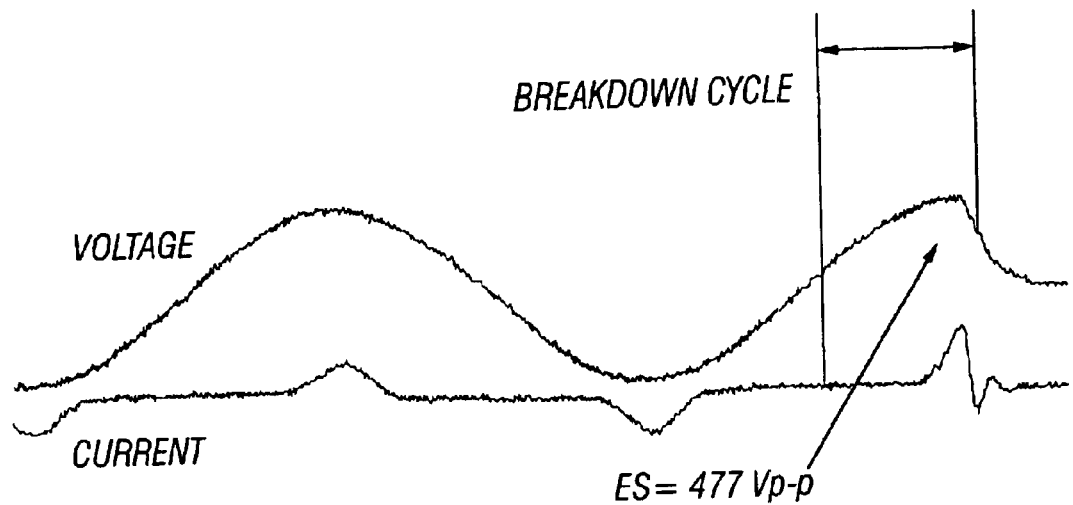
FIG. 1 is a graph showing the voltage and current waveforms versus time for an oil drilling fluid, where the current waveform exhibits the spiky form.

The method of the invention can be implemented with a general-purpose digital storage oscilloscope (DSO), attached to an ES meter, such as, for example, the FANN 23D, available from Halliburton Energy Services, Inc. in Houston, Tex. The DSO is connected with probes to the appropriate junctions in the circuit of the ES meter. This connection allows the DSO to accurately measure the voltage and current waveforms generated in the course of an ES test.

The circuitry of the ES meter performs six primary functions: power supply, test control, high voltage ramping AC sine wave generation, voltage measurement, break current threshold detection and ES voltage display. The sine wave generated by the ES meter starts at zero volts and increases, or ramps, at a steady rate. The ramping AC voltage is applied to the drilling fluid to be tested by means of a probe immersed in the fluid. The probe consists of two electrodes separated by a gap, and held by the electrically insulating body of the probe. In the preferred embodiment, the electrodes are flat, 0.125 inches in diameter, and separated by a 0.061-inch gap. When the probe is immersed in the drilling fluid, the gap is filled with the fluid.

One of the digital oscilloscope's probes is attached to the voltage sense circuit of the ES meter. Another is attached to the current sense circuit of the ES meter. Typically, this arrangement allows the apparatus to sense the voltage drop across a resistor, which is in series with the electrodes of the probe. The measured voltage will be directly proportional to the current passing through the resistor, in accordance with Ohm's Law. The trigger circuit of the DSO is connected to the break current detection circuit of the ES meter, where an abrupt change in the voltage indicates the instant of the break event. This break event occurs the instant that the current passing through the gap in the probe electrodes reaches 61 microamperes according to the API procedure, although the "true" break event may occur at other current levels. These connections to the ES meter must be made in such a manner that they do not interfere with the signals being measured. Preferably, the measurements are made at pressures and temperatures that simulate conditions in a subterranean wellbore.

During a test, the DSO stores rapid samples of the current and voltage waveform while the AC voltage is ramped up on the electrodes of the probe. Typically, these simultaneous samples would be taken at a rate of 0.5 million samples per second (0.5 MS/s) to allow sufficient resolution of the waveform. At a minimum, the current and voltage should be sampled simultaneously 250,000 times per second. The sample collection process is terminated by the DSO trigger circuit's detection of the break event. At this point, the digital samples can be transferred to a general-purpose personal computer (PC) by means of common interfaces, such as a serial or parallel connection, or a floppy disk.

The PC is used to analyze the collected waveforms. Preferably, the PC is programmed to calculate and store the Breakdown Energy for each waveform. For example, the Microsoft Excel® spreadsheet program can be used. In the preferred method, the stored samples representing the last cycle of the voltage waveform would be analyzed. Alternatively, more cycles leading up to the break event could be analyzed to characterize the fluid behavior. In the preferred method, the sampled waveforms would be processed to calculate the electrical energy expended to raise the current level to the threshold current in the last cycle. Alternatively, or additionally, other calculations could be performed. These might include, but are not limited to the harmonic distortion of the current waveform, the ratio of the ES to the break energy and the frequency distribution of the current waveform.

The described method is suitable for laboratory use. For field applications, it would be advantageous to combine all of the functions of the method, particularly the functions of waveform storage and processing, into one compact instrument. This could be accomplished by adding suitable computational and storage circuits to a redesigned ES meter. For example, it may be possible to use a class of integrated circuits referred to as digital signal processors (DSP) to process the waveforms in real time. Preferably, a field instrument would display the ES and the Breakdown Energy results in a compact form.

Many factors can influence the ES of a given drilling fluid. Such factors include, for example, without limitation, the type of base oil, the oil-water ratio, the salinity of the water phase, the size distribution of the water droplets in the oil phase, the types and size distribution of the solids suspended in the fluid, and the emulsifier type and concentration. Because of the many factors that can affect the ES reading, a single reading on a particular mud system is usually of limited usefulness. The trend seen from a number of ES meter readings for a particular mud system should preferably be used to make treatment decisions or decisions regarding possible use of the mud system for drilling in a subterranean formation. The method of the invention provides a more sensitive measurement for tracking these trends. The method of the invention provides not only the traditional API ES measurement (if desired), but also the Breakdown Energy measurement.

The ES measurement may be viewed as the electrical stress level at which the emulsion will break down. The Breakdown Energy measurement may be viewed as the energy that is applied to the emulsion to get it to break at the ES stress level. If the current waveform were always the same, the ES would be an excellent indicator of the energy requirements to break the emulsion. Hence, since the current waveform can vary, the Breakdown Energy provides a better indicator of the stability of the emulsion.

The more sinusoidal current waveform is associated with drilling fluids that are in good condition, i.e., that are strong enough that the emulsion is not likely to break and cause wetting of the formation during drilling. A drilling fluid with this type of waveform will yield higher Breakdown Energy measurements than a drilling fluid with a spikier current waveform with the same ES.

Figure 2:
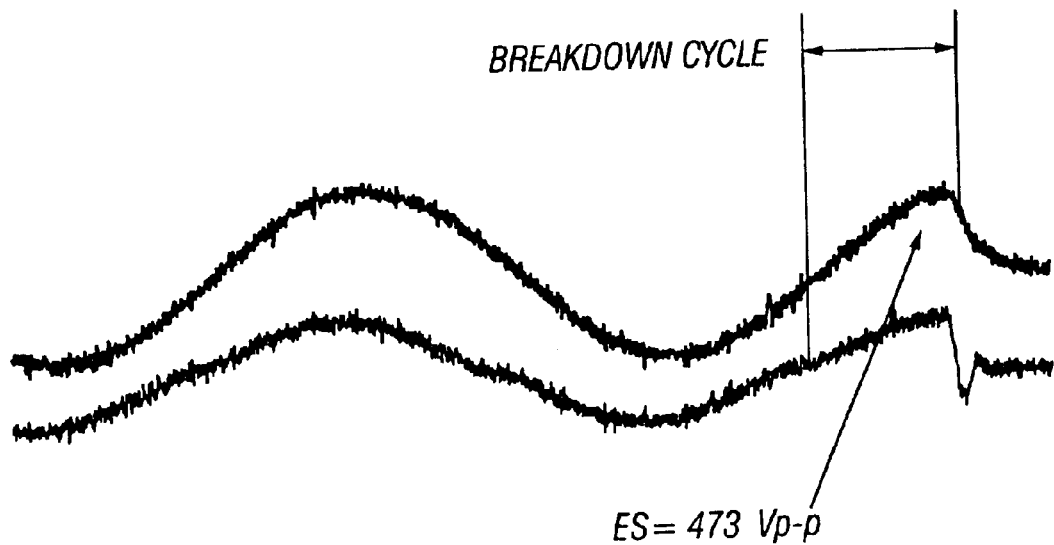
FIG. 2 is a graph showing the voltage and current waveforms versus time for a second oil drilling fluid, where the current waveform is almost sinusoidal.
Figure 3:
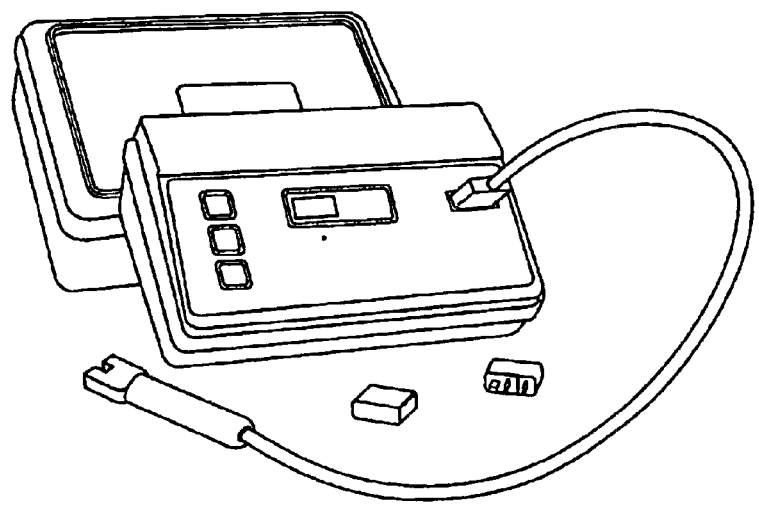
FIG. 3 is a view of the Fann Instrument Company, Model 23D Electrical Stability Tester (prior art) (website: http://www.fann.com/product_info_main.asp?catid=61)
Figure 4:
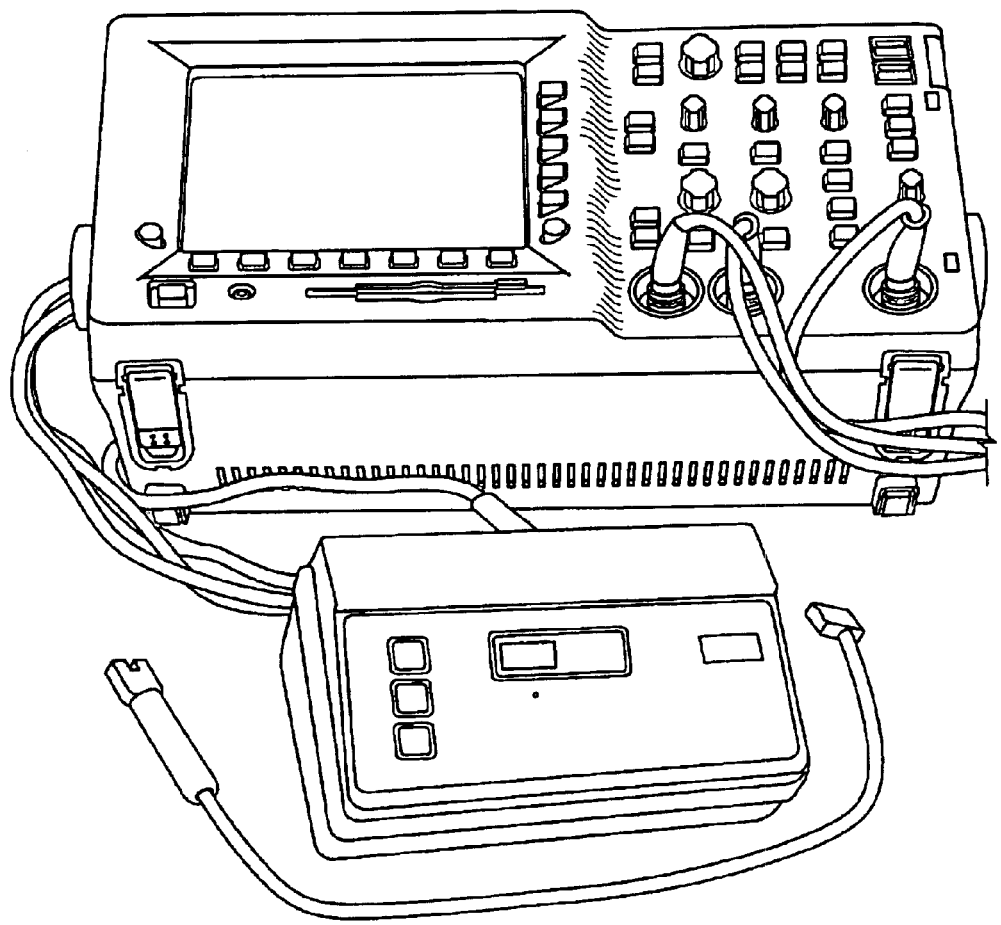
FIG. 4 is a view of a sample apparatus for use in the method of the invention.

The examples graphed in FIG. 1 and FIG. 2 are of two fluids exhibiting the same ES breakdown voltage (top curve), but having very different current waveforms (bottom curve). Using the conventional or traditional method of evaluating the fluids, that is, measuring the API ES, the fluids would be deemed identical, from an electrical stability standpoint, yet they are very different. In FIG. 1, the current is almost flat until immediately prior to breakdown, then the current rises sharply. In FIG. 2, the current is essentially proportional to voltage. In the second case, FIG. 2, more energy is expended breaking the emulsion, indicating a more stable and robust emulsion. The computed breakdown energy in these examples is 0.47 mJ and 1.73 mJ respectively.

The foregoing description of the invention is intended to be a description of preferred embodiments. Various changes in the details of the described method can be made without departing from the intended scope of this invention as defined by the appended claims.

We claim:

1. A method for characterizing an invert emulsion for use as a drilling fluid, said method comprising measuring the breakdown energy of said fluid, said measurement comprising analyzing current and voltage waveforms that occur prior to breakdown of said emulsion, said breakdown occurring when the current starts to rise rapidly and disproportionally faster than the voltage waveform.

2. The method of claim 1 wherein values from said breakdown energy are determined using the following equation:

$$\text{Breakdown Energy} \cong \sum i_k \times E_k \times (t_k - t_{k-1})$$

Where:

$i_{k=current}$
$E_{k=Voltage}$
$t_{k=Time}$
n=number of measurements.

3. The method of claim 1 further comprising measuring the electrical stability voltage of said fluid and measuring the breakdown energy and electrical stability of a second invert emulsion and comparing said breakdown energy measurements and said electrical stability voltage measurements of said fluids to determine which of the two fluids provides the stronger emulsion.

4. The method of claim 3 wherein said measurements of the electrical stability voltage and said measurements of the breakdown energy are made at pressures and temperatures that simulate conditions in the bore of a well.

5. The method of claim 3 wherein a digital oscilloscope is used to generate a voltage curve for each said breakdown energy measurement and an electrical current curve for each said breakdown energy measurement.

6. A method for evaluating an invert emulsion based drilling fluid for use in drilling a borehole in a subterranean formation, said method comprising:

measuring the voltage of said fluid until breakdown of said emulsion;

measuring the current of said fluid and charting the current signature of said fluid prior to said breakdown;

said breakdown occurring when the current starts to rise rapidly and disproportionally faster than the voltage waveform; and determining the breakdown cycle from said measurements.

7. The method of claim 6 wherein said charting of said current is done with an oscilloscope.

8. The method of claim 6 further comprising determining the breakdown energy for said emulsion.

9. A method for evaluating stability of an invert emulsion for use as a drilling fluid in drilling subterranean formations, said method comprising:

providing a sample of said fluid;

immersing a pair of electrodes in said sample;

applying a voltage-ramped, sinusoidal electrical signal across said pair of immersed electrodes, increasing said voltage over time until a threshold is reached;

while increasing said voltage, monitoring the voltage drop across said electrodes and monitoring the current across said electrodes and collecting and storing samples of the voltage waveforms and current waveforms;

after a threshold voltage is reached, processing said voltage waveforms and current waveforms to calculate the electrical energy expended to raise the current level to said threshold.

10. The method of claim 9 further comprising repeating all of the preceding steps with multiple samples of said fluid until a trend appears in said calculations.

11. The method of claim 9 wherein said threshold voltage is the voltage measured when the current reaches 61 $\mu$A.

12. The method of claim 9 wherein said threshold voltage is the voltage measured when the current starts rising disproportionally faster then the voltage.

13. The method of claim 9 wherein said samples of said voltage waveforms and current waveforms are taken at a rate of at least about 250,000 times per second.

14. The method of claim 13 wherein said samples of said voltage waveforms and current waveforms are taken simultaneously.

15. The method of claim 9 wherein said sampling of voltage waveforms and current waveforms discontinued after said threshold voltage is reached.

16. A method for assessing relative strength of at least two different invert emulsions, said method comprising measuring and comparing the breakdown energy for each emulsion, said measurement comprising analyzing current and voltage waveforms that occur prior to breakdown of each said emulsion, said breakdown occurring when the current starts to rise rapidly and disproportionally faster than the voltage waveform.

17. The method of claim 16 wherein said measurements are made while measuring the electrical stability of each emulsion.

* * * * *